(12) United States Patent
Lim et al.

(10) Patent No.: US 12,011,523 B2
(45) Date of Patent: Jun. 18, 2024

(54) VENTILATION SEAT OF VEHICLE

(71) Applicant: HYUNDAI TRANSYS INCORPORATED, Seosan-si (KR)

(72) Inventors: Ho Sub Lim, Hwaseong-si (KR); Sun Woo Kim, Hwaseong-si (KR); Tae Hyoung Yang, Hwaseong-si (KR); In Ho Lee, Hwaseong-si (KR); Hwa Jun Lee, Hwaseong-si (KR)

(73) Assignee: HYUNDAI TRANSYS INCORPORATED, Seosan-si (KR)

( * ) Notice: Subject to any disclaimer, the term of this patent is extended or adjusted under 35 U.S.C. 154(b) by 359 days.

(21) Appl. No.: 17/679,764

(22) Filed: Feb. 24, 2022

(65) Prior Publication Data

US 2022/0280678 A1 Sep. 8, 2022

(30) Foreign Application Priority Data

Mar. 5, 2021 (KR) .................. 10-2021-0029399

(51) Int. Cl.
*A61L 9/20* (2006.01)
*B60N 2/56* (2006.01)

(52) U.S. Cl.
CPC .............. *A61L 9/205* (2013.01); *B60N 2/56* (2013.01); *A61L 2209/21* (2013.01)

(58) Field of Classification Search
CPC .. A61L 9/205; A61L 2209/21; A61L 2209/16; B60N 2/56; B60N 2/565; B60N 2/5657; B60N 2/5635; B60N 2/5621; B60N 2/5642; B01D 53/007; B01D 53/86; B01D 2255/802; B01D 2259/804; B60H 3/0608; B60H 2003/0675; B60H 3/0071; B60H 3/06; A47C 7/744
See application file for complete search history.

(56) References Cited

U.S. PATENT DOCUMENTS

| | | | |
|---|---|---|---|
| 2017/0036516 A1* | 2/2017 | Kim | ............ B60H 3/0658 |
| 2021/0353819 A1* | 11/2021 | Iliffe-Moon | ............ A61L 9/205 |
| 2022/0280678 A1* | 9/2022 | Lim | ............ A61L 9/205 |
| 2022/0281284 A1* | 9/2022 | Lim | ............ B60H 1/00028 |
| 2023/0293762 A1* | 9/2023 | Yoo | ............ A61L 9/205 422/3 |

FOREIGN PATENT DOCUMENTS

| | | |
|---|---|---|
| CN | 105031702 A | 11/2015 |
| JP | 2017503708 A | 2/2017 |
| KR | 10-2010-0010265 A | 2/2010 |
| KR | 20120002300 A | 1/2012 |
| KR | 20120086809 A | 8/2012 |
| KR | 101851522 B1 | 4/2018 |

* cited by examiner

*Primary Examiner* — David A Vanore
(74) *Attorney, Agent, or Firm* — Bridgeway IP Law Group, PLLC; Jihun Kim

(57) ABSTRACT

A ventilation seat of a vehicle is proposed. The ventilation seat includes a ventilation pipe mounted in a seat of the vehicle and configured to suck indoor air and to discharge air toward a surface of the seat, a catalytic converter provided in an air flow path of the ventilation pipe, and configured to clean air passing through the air flow path when light is emitted, and a light source assembly provided on an inner wall of the air flow path of the ventilation pipe and arranged to face the catalytic converter to emit the light toward the catalytic converter.

10 Claims, 4 Drawing Sheets

VENTILATION SEAT OF VEHICLE

CROSS REFERENCE TO RELATED APPLICATION

The present application claims priority to Korean Patent Application No. 10-2021-0029399, filed Mar. 5, 2021, the entire contents of which is incorporated herein for all purposes by this reference.

BACKGROUND OF THE INVENTION

Field of the Invention

The present invention relates generally to a ventilation seat of a vehicle, wherein the ventilation seat is provided at a seat of the vehicle and configured to clean air passing through a ventilation pipe by using a photocatalyst when a ventilation function is operated and to discharge cleaned air toward a seating surface of the seat.

Description of the Related Art

Conventionally, general air conditioners and heaters are used for air conditioning in a vehicle. Furthermore, a ventilation seat for convenience of each occupant is widely used. The ventilation seat discharges gas from a seating surface of the seat, thereby cooling the seat in direct contact with the occupant.

On the other hand, when air inside the vehicle is polluted with microorganisms, nitrogen oxides, exhaust gas, fine dust, odors, etc. due to occupant's use of the vehicle or the indoor and outdoor environment of the vehicle, the above pollution adversely affects the occupant. Thus, the importance of technology related to air cleaning in a vehicle is increasing recently.

In order to solve the above problem, a filter for air cleaning can be provided inside the ventilation seat, but a type of filter used in the ventilation seat, amount of filter, a location of filter, etc. may be limited due to characteristics of the ventilation seat that should be driven with low power and low noise. Therefore, it is necessary to develop a seat air conditioning system that minimizes the above problems and has high air cleaning efficiency.

The foregoing described as the controller and the controlling method of operating a fuel cell is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problem occurring in the related art, and the present invention is intended to provide a ventilation seat of a vehicle, wherein the ventilation seat is provided in a seat of the vehicle and is configured to emit UV rays to a photocatalyst in operation of a ventilation function to clean air passing through a ventilation pipe and to discharge cleaned air toward a seating surface of the seat.

In order to achieve the above objective, according to one aspect of the present invention, there is provided a ventilation seat of a vehicle, the ventilation seat including: a ventilation pipe mounted in a seat of the vehicle and configured to suck indoor air and to discharge air toward a surface of the seat; a catalytic converter provided in an air flow path of the ventilation pipe, and configured to clean air passing through the air flow path when light is emitted; and a light source assembly provided on an inner wall of the air flow path of the ventilation pipe and arranged to face the catalytic converter to emit the light toward the catalytic converter.

A material containing a photocatalyst may be put on the catalytic converter, and as the light emitted from the light source assembly reaches to the photocatalyst, air may be cleaned.

The catalytic converter may be provided in a location within the inner wall or on a side wall of the air flow path of the ventilation pipe, and be arranged in a direction in which air flows.

The light source assembly may include at least one light source, the at least one light source may be arranged in a direction in which air flows and be configured to emit the light containing UV rays to the catalytic converter.

The light source assembly may include at least one light source, and the at least one light source may be configured to emit the light over an entire surface of the catalytic converter facing the at least one light source.

The light source assembly may include at least one light source, and number or a location of the at least one light source may be determined in response to an inner width of the air flow path of the ventilation pipe or a size of the catalytic converter.

An expansion part may be provided in the air flow path of the ventilation pipe in a direction in which air flows, the expansion part being shaped such that the air flow path expands and contracts, and the catalytic converter may be provided in the expansion part.

The light source assembly may include a plurality of light sources provided on an inner wall of the expansion part, and the catalytic converter may be arranged in a width direction of the air flow path of the ventilation pipe.

The catalytic converter may be formed in a porous structure, and when the plurality of light sources may emit light, air passing through an inside portion of the catalytic converter may be cleaned.

The ventilation pipe may be provided at a seatback or a seat cushion, and be configured to suck indoor air through a blower provided at the seat or to discharge cleaned air toward the seatback or the seat cushion.

According to the ventilation seat of a vehicle of the present invention, the ventilation pipe is provided in the seat of the vehicle and UV rays are emitted to the photocatalyst when the ventilation function is operated, so that air flowing through the air flow path of the ventilation pipe can be cleaned and the cleaned air can be discharged to the seating surface of the seat.

BRIEF DESCRIPTION OF THE DRAWINGS

The above and other objectives, features, and other advantages of the present invention will be more clearly understood from the following detailed description when taken in conjunction with the accompanying drawings, in which.

DETAILED DESCRIPTION OF THE INVENTION

Figure 1:
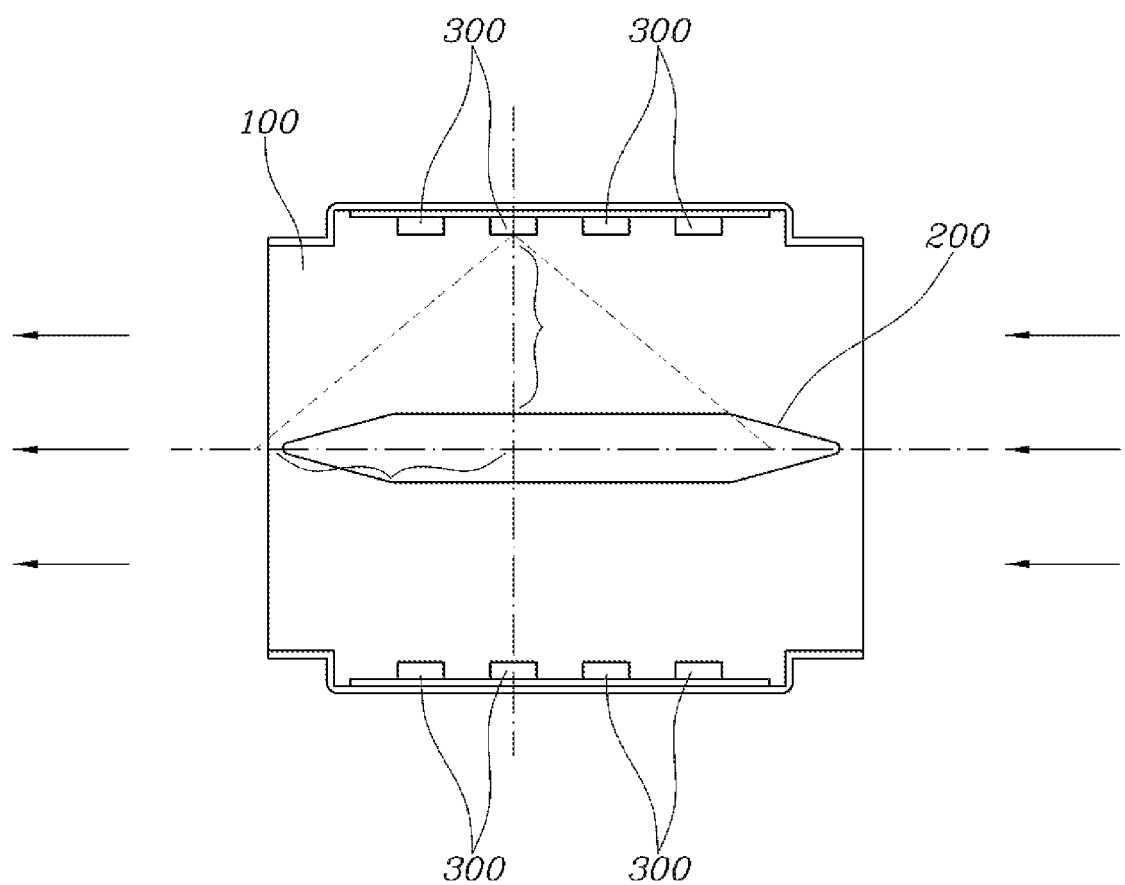
FIG. 1 is a view showing a ventilation seat of a vehicle according to an embodiment of the present invention, wherein a catalytic converter is located at a location within an inner wall of an air flow path of a ventilation pipe.
Figure 2:
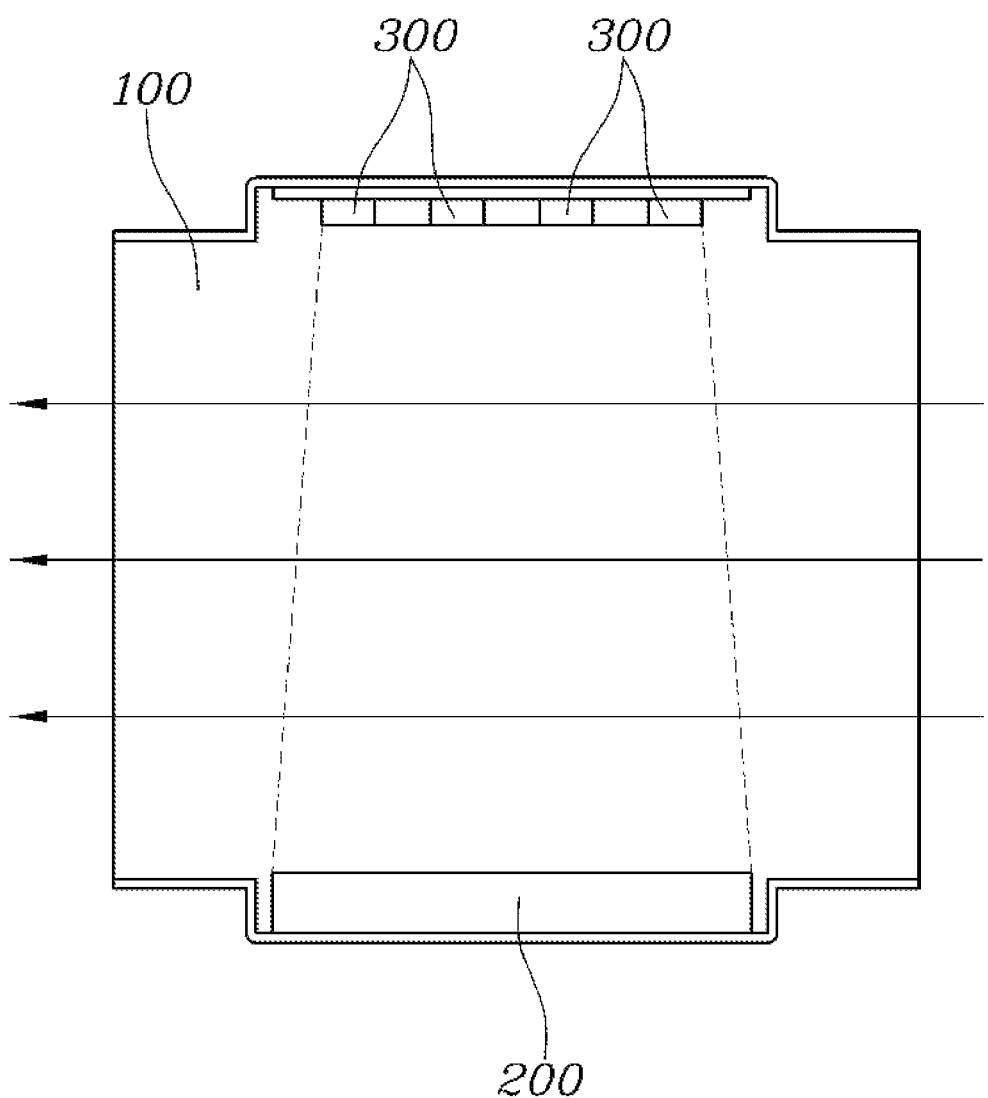
FIG. 2 is a view showing the ventilation seat of a vehicle according to an embodiment of the present invention, wherein the catalytic converter is located on an inner side wall of the air flow path of the ventilation pipe.
Figure 3:
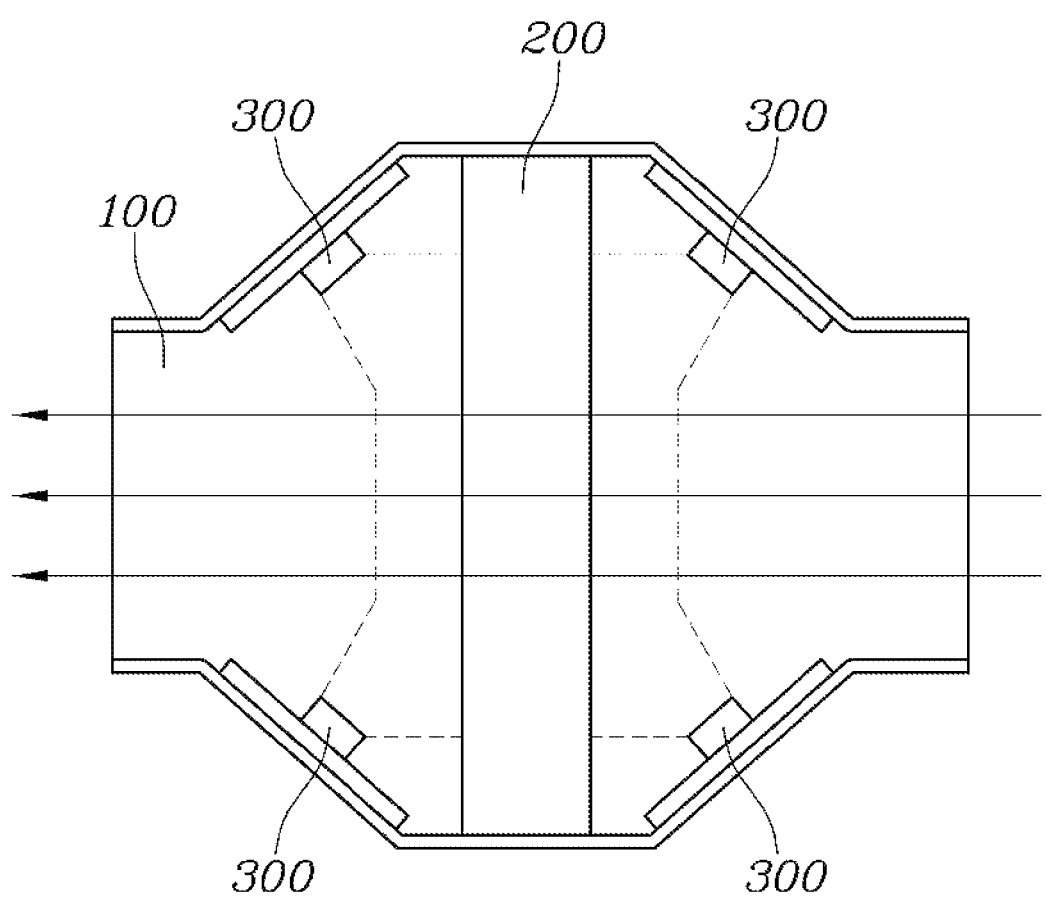
FIG. 3 is a view showing the ventilation seat of a vehicle according to an embodiment of the present invention, wherein an expansion part is shaped such that the air flow path of the ventilation pipe expands and contracts.
Figure 4:
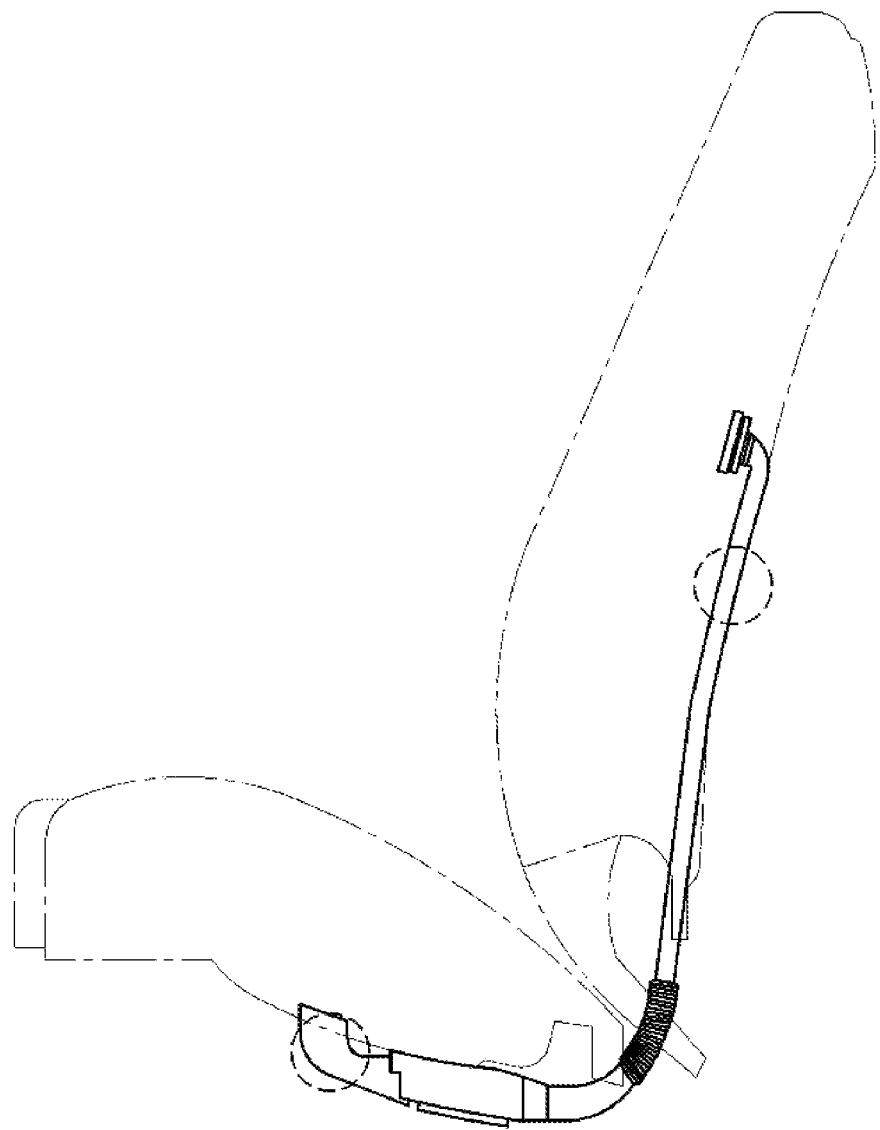
FIG. 4 is a view showing the ventilation seat of a vehicle according to an embodiment of the present invention, wherein the ventilation pipe is located in a seat cushion or a seatback.

FIG. 1 is a view showing a ventilation seat of a vehicle according to an embodiment of the present invention, wherein a catalytic converter is located at a location within an inner wall of an air flow path of a ventilation pipe. FIG. 2 is a view showing the ventilation seat of a vehicle according to an embodiment of the present invention, wherein the catalytic converter is located on an inner side wall of the air flow path of the ventilation pipe. FIG. 3 is a view showing the ventilation seat of a vehicle according to an embodiment of the present invention, wherein an expansion part is shaped such that the air flow path of the ventilation pipe expands and contracts. FIG. 4 is a view showing the ventilation seat of a vehicle according to an embodiment of the present invention, wherein the ventilation pipe is located in a seat cushion or a seatback.

FIG. 1 is a view showing a ventilation seat of a vehicle according to an embodiment of the present invention, wherein a catalytic converter is located at a location within an inner wall of an air flow path of a ventilation pipe. According to the embodiment of the present invention, the ventilation seat of a vehicle includes: a ventilation pipe 100 mounted to a seat of the vehicle and configured to suck indoor air and to discharge air to a surface of the seat; a catalytic converter 200 provided in an air flow path of the ventilation pipe 100, and configured to clean air passing through the air flow path when light is emitted; and a light source assembly 300 provided on an inner wall of the air flow path of the ventilation pipe 100, and arranged to face the catalytic converter 200 to emit light toward the catalytic converter 200.

The ventilation seat of a vehicle according to the embodiment of the present invention is provided in each seat and serves as an air cleaner of a vehicle such that air is discharged to the seating surface of the seat through the ventilation pipe 100 and while polluted air in the vehicle room is cleaned (sterilized, deodorized, etc.) by the catalytic converter 200. A first end of the air flow path to which the ventilation pipe 100 is connected includes a blower. The vehicle indoor air is sucked into the ventilation pipe 100 through the blower, and the air is cleaned while passing through the ventilation pipe 100, and cleaned air is guided to a seat cushion or a seatback to be discharged to the seating surface of the seat.

Meanwhile, according to the embodiment of the present invention, a material containing a photocatalyst is put on the catalytic converter 200 of the ventilation seat of a vehicle, and as light emitted from the light source assembly 300 reached the photocatalyst, the air may be cleaned.

Specifically, the photocatalyst is a compound that absorbs light energy to initiate a photochemical reaction and promotes a photochemical reaction as a catalyst. When light is emitted, the photocatalyst has effects such as sterilization or deodorization. Herein, the light source assembly 300 may consist of an LED module, and the LED module is a device that splits light waves with a wavelength of 380 nm or less and emits light at an UV-A level. The photocatalyst may be titanium oxide (TiO2). A plurality of light sources 300 is provided to face the catalytic converter 200 in the inside of the air cleaning module 100 while having predetermined spectral angles (e.g., 120 degrees). Therefore, the plurality of light sources 300 may emit light over the entire surface of the catalytic converter 200 to increase air cleaning efficiency.

FIG. 2 is a view showing the ventilation seat of a vehicle according to an embodiment of the present invention, wherein the catalytic converter is located on an inner side wall of the air flow path of the ventilation pipe. In the ventilation seat of a vehicle according to the embodiment of the present invention, the catalytic converter 200 is provided in a location within the inner wall or an inner side wall of the air flow path of the ventilation pipe 100, and is arranged in a direction in which air flows.

In detail, referring to FIGS. 1 to 3, a dotted line reaching from the light source assembly 300 to the catalytic converter 200 indicates the range that light of the light source assembly 300 reaches. The catalytic converter 200 is provided on the location within the inner walls or the inner side wall of the air flow path when necessary, and the light source assembly 300 also may be provided on each inner wall or a second inner side wall opposite to the inner side wall with the catalytic converter 200. Furthermore, when the shape of the ventilation pipe 100 is a circular shape such as a pipe, the catalytic converter 200 is located at the location within the inner wall of the air flow path, and the light source assembly 300 are arranged in a circular shape along the inner wall of the air flow path so that light is emitted toward the catalytic converter 200 at 360 degrees from the light source assembly 300.

Furthermore, according to the embodiment of the present invention, at least one light source 300 is provided in the ventilation seat of a vehicle, and the at least one light source part 300 is arranged in the direction in which air flows, thereby emitting the light including UV rays toward the catalytic converter 200. The at least one the light source part 300 is provided, and the at least one light source part 300 may emit the light over the entire surface of the catalytic converter 200, the surface facing the light source assembly 300. As the at least one light source part 300 emits the light over the entire surface of the catalytic converter 200, air passing through the catalytic converter 200 is cleaned and air cleaning efficiency is increased.

Meanwhile, according to the embodiment of the present invention, the at least one light source part 300 is provided in the ventilation seat of a vehicle, and the number or a location of the at least one light source part 300 may be determined in response to the inner width of the air flow path of the ventilation pipe 100 or the size of the catalytic converter 200. Referring to FIG. 1, the maximum spectral angle (120 degrees) of the light source assembly 300 is determined and the at least one light source part 300 is provided on the inner wall of the air flow path of the ventilation pipe 100. Therefore, when the width of the air flow path of the ventilation pipe 100 and the location of the catalytic converter 200 according to the air flow path width are changed, the number or location of the at least one light source part 300 should be determined so as to sufficiently emit the light toward the catalytic converter 200.

Furthermore, in order to increase the air cleaning efficiency with a minimum number of the light source assembly 300, considering the maximum spectral angle of the light source assembly 300 in response to the size of the catalytic converter 200, the at least one light source part 300 is arranged on the inner wall of the air flow path of the ventilation pipe 100, thereby emitting the light over the entire area of the catalytic converter 200.

Meanwhile, referring to FIG. 1, using the Pythagorean theorem, the optimal catalyst length compared to a duct cross section may be converted as tan 30°=0.5*catalyst length/0.5*duct length, and the optimal catalyst length may be derived as 'duct length=0.577*catalyst length'. Therefore, based on the minimum number of the light source assembly 300, the increase in cost due to technological application may be minimized with a minimal amount of catalyst.

FIG. 3 is a view showing the ventilation seat of a vehicle according to an embodiment of the present invention, wherein an expansion part is shaped such that the air flow path of the ventilation pipe expands and contracts. According to the embodiment of the present invention, the ventilation pipe 100 of the ventilation seat of a vehicle has an expansion part (no reference numeral) in the air flow path thereof. The expansion part is formed such that the air flow path expands and contracts in the direction in which air flows. The catalytic converter 200 may be provided in the expansion part. Therefore, the plurality of light sources 300 is provided on an inner wall of the expansion part, and the catalytic converter 200 may be arranged in a width direction of the air flow path of the ventilation pipe 100.

Referring to FIG. 3, unlike as shown in FIGS. 1 and 2, the catalytic converter 200 is arranged in the width direction crossing the air flow path of the ventilation pipe 100, so that a contact area in contact with the catalytic converter 200 is significantly increased. Herein, the catalytic converter 200 is formed in a porous structure. When the light is emitted from the light source assembly 300, air passing through the inside of the catalytic converter 200 may be cleaned.

Furthermore, when the air flow path expands, a flow rate of air passing through the ventilation pipe 100 is reduced at the expansion part, and thus the air cleaning efficiency of air passing through the catalytic converter 200 may be increased. Meanwhile, the catalytic converter 200 is formed in a structure such as the porous structure minimizing air resistance, thereby minimizing the effect on ventilation performance of the catalytic converter 220 in operation of the ventilation seat.

FIG. 4 is a view showing the ventilation seat of a vehicle according to an embodiment of the present invention, wherein the ventilation pipe is located in a seat cushion or a seatback. According to the embodiment of the present invention, the ventilation pipe 100 of the ventilation seat of a vehicle is provided in the seatback or the seat cushion, and is configured to suck indoor air or to discharge cleaned air through a blower provided in the seat to a surface of the seatback or the seat cushion. Referring to FIG. 4, the blower is provided at a lower end of the seat cushion, and air sucked through the blower is discharged to the seat cushion or the seatback through a separate air flow path. The ventilation pipe 100 is provided on a flow path connected to the seat cushion or the seatback, thereby discharging cleaned air to the seat cushion or the seatback.

Although the preferred embodiment of the present invention has been disclosed for illustrative purposes, those skilled in the art will appreciate that various modifications, additions, and substitutions are possible, without departing from the spirit and scope of the present invention.

What is claimed is:

1. A ventilation seat of a vehicle, the ventilation seat comprising:
    a ventilation pipe mounted in a seat of the vehicle and configured to suck air and to discharge the air toward a surface of the seat;
    a catalytic converter provided in an air flow path of the ventilation pipe, and configured to clean the air passing through the air flow path when light is emitted; and
    a light source assembly provided on an inner wall of the air flow path of the ventilation pipe and arranged to face the catalytic converter to emit the light toward the catalytic converter.

2. The ventilation seat of claim 1, wherein a material containing a photocatalyst is put on the catalytic converter, and as the light emitted from the light source assembly reaches to the photocatalyst, the air is cleaned.

3. The ventilation seat of claim 1, wherein the catalytic converter is provided in a location within the inner wall or on a side wall of the air flow path of the ventilation pipe, and is arranged in a direction in which the air flows.

4. The ventilation seat of claim 1, wherein the light source assembly comprises at least one light source, the at least one light source is arranged in a direction in which the air flows and is configured to emit the light containing UV rays to the catalytic converter.

5. The ventilation seat of claim 1, wherein the light source assembly comprises at least one light source, and the at least one light source is configured to emit the light over an entire surface of the catalytic converter facing the at least one light source.

6. The ventilation seat of claim 1, wherein the light source assembly comprises at least one light source, and number or a location of the at least one light source is determined in response to an inner width of the air flow path of the ventilation pipe or a size of the catalytic converter.

7. The ventilation seat of claim 1, wherein an expansion part is provided in the air flow path of the ventilation pipe in a direction in which the air flows, the expansion part being shaped such that the air flow path expands and contracts, and the catalytic converter is provided in the expansion part.

8. The ventilation seat of claim 7, wherein the light source assembly comprises a plurality of light sources provided on an inner wall of the expansion part, and the catalytic converter is arranged in a width direction of the air flow path of the ventilation pipe.

9. The ventilation seat of claim 8, wherein the catalytic converter is formed in a porous structure, and when the plurality of light sources emits light, the air passing through an inside portion of the catalytic converter is cleaned.

10. The ventilation seat of claim 1, wherein the ventilation pipe is provided at a seatback or a seat cushion, and is configured to suck the air through a blower provided at the seat or to discharge the cleaned air toward the seatback or the seat cushion.

* * * * *